United States Patent

Konz

Patent Number: 5,391,541
Date of Patent: Feb. 21, 1995

[54] HERBICIDAL 3-(SUBSTITUTED-BENZYL)-1-METHYL-6-TRIFLUOROMETHYLURACILS

[75] Inventor: Marvin J. Konz, Yardley, Pa.

[73] Assignee: FMC Corporation, Philadelphia, Pa.

[21] Appl. No.: 224,423

[22] Filed: Apr. 8, 1994

Related U.S. Application Data

[63] Continuation-in-part of Ser. No. 105,075, Aug. 11, 1993, abandoned.

[51] Int. Cl.$^6$ ............... A01N 43/54; C07D 239/55
[52] U.S. Cl. .................. 504/243; 544/309; 544/311; 544/312; 544/314
[58] Field of Search ............ 544/309, 312, 311, 314; 504/243

[56] References Cited

U.S. PATENT DOCUMENTS

| | | | |
|---|---|---|---|
| 3,235,357 | 2/1966 | Loux | 504/243 |
| 3,235,358 | 2/1966 | Soboczenski | 504/243 |
| 3,235,360 | 2/1966 | Soboczenski | 504/243 |
| 3,235,361 | 2/1966 | Loux | 504/243 |
| 3,235,362 | 2/1966 | Ellis | 504/243 |
| 3,235,363 | 2/1966 | Luckenbaugh et al. | 504/243 |
| 3,352,862 | 11/1967 | Loux | 504/243 |
| 3,352,863 | 11/1967 | Soboczenski | 504/243 |
| 3,360,521 | 12/1967 | Soboczenski | 504/243 |
| 3,360,522 | 12/1967 | Loux | 504/243 |
| 3,580,913 | 3/1971 | Lutz | 504/243 |
| 5,162,326 | 11/1992 | Naka et al. | 544/309 |
| 5,298,481 | 3/1994 | Tice | 544/309 |

FOREIGN PATENT DOCUMENTS 50-25144  2/1993  Japan.
5025142   2/1993  Japan.

*Primary Examiner*—Cecilia Tsang
*Attorney, Agent, or Firm*—H. Robinson Ertelt; Robert M. Kennedy

[57] ABSTRACT

Herbicidal 3-(substituted-benzyl)-1-methyl-6-trifluoromethyluracils, compositions containing them, and methods of using them to control undesired plant growth, including use to control weeds in certain crops, are disclosed. The herbicidal compounds of the present invention are defined by the following generic structure:

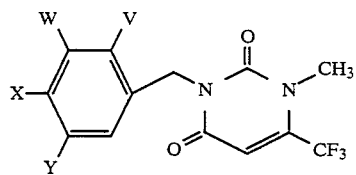

in which V is hydrogen or halogen; W is hydrogen, halogen, lower alkoxy, lower alkylaminocarbonyl, propargyloxy, or cyano; X is hydrogen or chlorine; and Y is hydrogen, halogen, cyano, lower alkylaminocarbonyl, or carboxy.

23 Claims, No Drawings

HERBICIDAL 3-(SUBSTITUTED-BENZYL)-1-METHYL-6-TRIFLUOROMETHYLURACILS

This application is a CIP of U.S. Ser. No. 08/105,075, filed Aug. 11, 1993, now abandoned.

The invention described in this application pertains to weed control in agriculture, horticulture, and other fields where there is a desire to control unwanted plant growth. More specifically, the present application describes certain herbicidal 3-( substituted-benzyl)-1-methyl-6-trifluoromethyluracils, as well as compositions containing them, methods of preparing them, and methods for preventing or destroying undesired plant growth by preemergence or postemergence application of herbicidal compositions to the locus where control is desired. The herbicidal activity of the present compounds, particularly the use of compounds of this class to control undesired plant growth in the presence of certain crops, has not previously been described.

The use of uracils as herbicides has previously been reported. U.S. Pat. Nos. 3,235,357, 3,235,358, 3,235,360, 3,235,361, 3,235,363, 3,352,862, 3,352,863, 3,360,521, and 3,360,522, all disclose and claim a wide variety of substituted uracils for use as herbicides. Of these, only 3,235,363 discloses uracils with a substituent in the 1-position. The patents disclose that certain of the disclosed compounds may be used to control undesired plant growth in the presence of specified crops, but there is no suggestion as to how one might determine which compounds are selective and which are not. Despite the extremely broad disclosures of these patents, none appears to disclose the genus of the compounds of the present invention.

Japanese Kokai Nos. 05025142 and 05025144 disclose a number of insecticidal and acaracidal, substituted uracils.

U.S. Pat. No. 3,580,91 3 discloses and claims a process for the preparation of herbicidal substituted-6-trifluoromethyluracils, the genus of which differs from that of the present invention only in being unsubstituted at the 1-position.

Nothing in these cited patents, or in any reference of which applicant is aware, makes obvious the compounds of this invention, particularly the criticality of the substitution pattern of the phenyl ring that results in the high degree of herbicidal activity of the preferred compounds.

It has now been found that certain 3-(substituted-benzyl)-1-methyl-6-trifluoromethyluracil compounds are highly active herbicides. The novel compounds of the present invention are defined by the following generic structure:

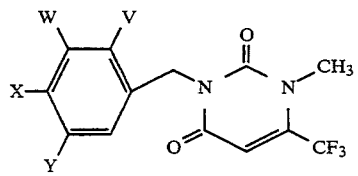

in which V is hydrogen or halogen;

W is hydrogen, halogen, lower alkoxy, lower alkylaminocarbonyl, propargyloxy, or cyano;

X is hydrogen or chlorine;

Y is hydrogen, halogen, cyano, lower alkylaminocarbonyl, or carboxy, where halogen is bromine, chlorine, fluorine, or iodine, and lower means having one to three carbon atoms.

Preferred are those compounds in which V is hydrogen or chlorine, W is hydrogen, chlorine, lower alkoxy, lower alkylaminocarbonyl, propargyloxy, or cyano, Y is hydrogen, chlorine, iodine, cyano, lower alkylaminocarbonyl, or carboxy, and lower means having one or two carbon atoms.

Particularly preferred are those compounds in which V is chlorine, and (1) W is chlorine, and X and Y are both hydrogen, (2) W is chlorine, iodine, methoxy, or cyano, and one of X and Y is chlorine, or (3) W is chlorine, X is hydrogen, and Y is iodine, cyano, or ethylaminocarbonyl.

The compounds of the present invention were prepared by methods known in the art. U.S. Pat. No. 3,580,913 discloses a process for preparing 3-substituted-6-trifluoromethyluracils unsubstituted in the 1-position. U.S. Patent 3,235,363 also discloses the preparation of 3-substituted uracils and in addition shows their conversion to 1-substituted uracils. The following examples are illustrative of the manner in which compounds of the class herein disclosed may be prepared.

EXAMPLE 1

SYNTHESIS OF 1-METHYL-3-(2,3,5-TRICHLOROPHENYLMETHYL)-6-TRIFLUOROMETHYLURACIL (COMPOUND 14)

Step A Synthesis of 2,3,5-trichlorophenylmethanol as an intermediate

A suspension of 5.5 grams (0.144 mole) of lithium aluminum hydride in 300 mL of diethyl ether was stirred, and 25.0 grams (0.111 mole) of 2,3,5-trichlorobenzoic acid in 200 mL of diethyl ether was added dropwise at a rate which maintained a gentle reflux. The complete addition required about 75 minutes. Upon completion of addition, the reaction was mixture heated at reflux for 4.5 hours. After this time the reaction mixture was stirred for about 16 hours, during which time it was allowed to cool to ambient temperature. The reaction mixture was then cooled to below 10° C., and 6 mL of water was added slowly dropwise. Upon completion of addition, 5 mL of aqueous 20% sodium hydroxide was added dropwise, followed by an additional 12 mL of water added dropwise. The reaction mixture was then stirred for 20 minutes and filtered through diatomaceous earth. The filtrate was concentrated under reduced pressure to a residue. The residue was stirred into water, and the combination was extracted with ethyl acetate. The extracts were combined and washed with three portions of water. The organic layer was dried with sodium sulfate and filtered. The filtrate was concentrated under reduced pressure, yielding 17.1 grams of 2,3,5-trichlorophenylmethanol. The NMR spectrum was consistent with the proposed structure.

Step B Synthesis of 2,3,5-trichlorophenylmethyl bromide as an intermediate

A solution of 7.6 grams (0.028 mole) of phosphorus tribromide in 200 mL of toluene was stirred, and 17.0 grams (0.080 mole) of 2,3,5-trichlorophenylmethanol was washed into the reaction vessel with about 5 mL of toluene. Upon completion of addition, the reaction mixture was stirred at ambient temperature for about 16 hours. The reaction mixture was then concentrated under reduced pressure to a residue. The residue was dissolved in ethyl acetate and washed with three portions of water. The organic layer was dried with sodium sulfate and filtered. The filtrate was concentrated under reduced pressure, yielding 21.2 grams of 2,3,5-trichlorophenylmethyl bromide. The NMR spectrum was consistent with the proposed structure.

Step C Synthesis of 2,3,5-trichlorophenylacetonitrile as an intermediate

A solution of 19.2 grams (0.070 mole) of 2,3,5-trichlorophenylmethyl bromide in 50 mL of methanol was stirred, and a solution of 4.1 grams (0.084 mole) of sodium cyanide in 10 mL of water was added dropwise during a 10 minute period. The addition caused an exothermic reaction which raised the reaction mixture temperature to about 35° C. Upon completion of addition, the reaction mixture was warmed to reflux, where it was stirred for 4.5 hours. The reaction mixture was allowed to cool to ambient temperature, where it was stirred for about 60 hours. After this time the reaction mixture was poured into water, and the mixture was extracted with ethyl acetate. The extract was washed with two portions of water, two 25 mL portions of aqueous 10% hydrochloric acid, and then with three portions of water. The organic layer was dried with sodium sulfate and filtered. The filtrate was concentrated under reduced pressure, yielding 10.8 grams of 2,3,5-trichlorophenylacetonitrile. The infrared spectrum was consistent with the proposed structure.

Step D Synthesis of 2,3,5-trichlorophenylacetic acid as an intermediate

A mixture of 6.9 grams (0.031 mole) of 2,3,5-trichlorophenylacetonitrile and 65 mL of water was stirred, and 65 mL of concentrated sulfuric acid was cautiously added. Upon completion of addition, the reaction mixture was heated to reflux, where it was stirred for about 2 hours. After this time the reaction mixture was cooled in an ice-bath and filtered. The collected solid was washed with water and then dissolved in ethyl acetate. The organic layer was washed with two portions of water and then with one portion of an aqueous solution saturated with sodium chloride. The organic layer was then dried with sodium sulfate and filtered. The filtrate was concentrated under reduced pressure, yielding 6.3 grams of 2,3,5-trichlorophenylacetic acid, mp 125°–133° C. The NMR spectrum was consistent with the proposed structure.

Step E Synthesis of 2,3,5-trichlorophenylacetyl chloride as an intermediate

A suspension of 6.0 grams (0.023 mole) of 2,3,5-trichlorophenylacetic acid in about 125 mL of carbon tetrachloride was stirred, and 5 mL of thionyl chloride was added. The reaction mixture was then warmed to reflux, where it was stirred for about 30 minutes. After this time the reaction mixture was concentrated under reduced pressure, yielding 6.4 grams of 2,3,5-trichlorophenylacetyl chloride.

Step F Synthesis of 2,3,5-trichlorophenylmethyl isocyanate as an intermediate

A suspension of 6.4 grams (0.025 mole) of 2,3,5-trichlorophenylacetyl chloride in 50 mL of toluene was stirred, and 10 drops of triethylamine was added. The reaction mixture was warmed to reflux, and 3.1 grams (0.027 mole) of azidotrimethylsilane was added dropwise. Upon completion of addition, the reaction mixture was heated at reflux for about 15 minutes. After this time the reaction mixture was cooled and concentrated under reduced pressure to a residue. The residue was distilled under high vacuum, yielding in one fraction, 3.2 grams of 2,3,5-trichlorophenylmethyl isocyanate, bp 95°–110° C./0.04 mm Hg. The infrared spectrum was consistent with the proposed structure, but indicated the presence of some impurities.

An alternative synthesis route to this intermediate starts with 2,4-dichloro-6-methylaniline, which is reacted with tert-butyl nitrite in acetonitrile to give the intermediate diazonium compound in the presence of copper(II) chloride, yielding 2,3,5-trichlorotoluene. Bromination of this intermediate is carried out in carbon tetrachloride with bromosuccinimide and ultraviolet illumination, yielding the corresponding phenylmethyl bromide. Potassium phthalimide is then reacted with the phenylmethyl bromide in N,N-dimethylformamide, producing the corresponding N-(substituted phenylmethyl)-phthalimide. This phthalimide is dissolved in ethanol, and hydrazine hydrate is added to the solution, which is then heated to reflux. Cooling, adding aqueous hydrochloric acid, and further heating of the reaction mixture at reflux yields the corresponding phenylmethylamine. Reacting the phenylmethylamine with trichloromethyl chloroformate in the presence of powdered carbon by the method described in Japanese Kokai 78 18,515 yields the corresponding substituted phenylmethyl isocyanate, 2,3,5-trichlorophenylmethyl isocyanate.

Step G Synthesis of 3-(2,3,5-trichlorophenylmethyl)-6-trifluoromethyl uracil as an intermediate Under a nitrogen atmosphere, a stirred suspension of 0.62 gram (0.01 5 mole) of 60% sodium hydride (in mineral oil) in 30 mL of N,N-dimethylformamide was cooled to below 7° C., and a solution of 2.8 grams (0.015 mole) of ethyl 3-amino-4,4,4-trifluoro-2-butenoate in 15 mL of N,N-dimethylformamide was added dropwise at a rate to maintain the reaction mixture below 7° C. Upon completion of addition, the reaction mixture was stirred for about 45 minutes, during which time the reaction mixture temperature was about 2°–4° C. After this time a solution of 3.2 grams of 2,3,5-trichlorophenylmethyl isocyanate in 10 mL of N,N-dimethylformamide was added dropwise at a rate to maintain the reaction mixture temperature at about 2°–4° C. Upon completion of addition, the reaction mixture was stirred for about 10 minutes at 2°–4° C. and then warmed to 70°–85° C., where it was stirred for 3 hours. After this time the reaction mixture was allowed to cool to ambient temperature, where it stirred for about 16 hours. The reaction mixture was then poured into water, and the mixture was extracted with ethyl acetate. The extract was then washed with one portion of water. The water layer and the wash were combined and acidified with concentrated hydrochloric acid. The resultant solid was collected by filtration, yielding, when dried, 0.5 gram of solid. To collect additional product, the ethyl acetate extract was again washed, this time with five 150 mL portions of water. The combined washes were acidified with concentrated hydrochloric acid. The resultant solid was collected by filtration. The solid was dissolved in ethyl acetate and washed with water. The organic layer was dried with sodium sulfate and filtered. The filtrate was concentrated under reduced pressure, yielding a solid residue. The solid was combined with the 0.5 gram of material collected above, yielding 2.7 grams of 3-(2,3,5-trichlorophenylmethyl)-6-trifluoromethyluracil, mp 199°–202° C. The NMR spectrum was consistent with the proposed structure.

A variation in the synthesis route to intermediates such as that produced by Step G above begins with an appropriately substituted phenylmethylamine, which is reacted with ethyl chloroformate in the presence of triethylamine, producing the corresponding ethyl N-(substituted phenylmethyl) carbamate. Reaction of the ethyl N-(substituted phenylmethyl) carbamate with ethyl 3-amino-4,4,4-trifluoro-2-butenoate in the presence of sodium hydride yields the corresponding 3-(substituted phenylmethyl)-6-trifluoromethyluracil, which may then be methylated in the manner described below in Example 1, Step H.

Step H Synthesis of 1-methyl-3-(2,3,5-trichlorophenylmethyl)-6-trifluoromethyluracil (Compound 14)

A solution of 2.4 grams (0.007 mole) of 3-(2,3,5-trichlorophenylmethyl)-6-trifluoromethyluracil in 60 mL of acetone was stirred, and 1.8 grams (0.013 mole) of potassium carbonate, followed by 1.8 grams (0.010 mole) of dimethyl sulfate were added. Upon completion of addition, the reaction mixture was warmed to reflux, where it was stirred for about 2 hours. The reaction mixture was then cooled and poured into water. The mixture was extracted with ethyl acetate. The extract was washed with three portions of water and then with one portion of an aqueous solution saturated with sodium chloride. The organic layer was dried with sodium sulfate and filtered. The filtrate was concentrated under reduced pressure to a residue. The residue was subjected to column chromatography on silica gel. Elution was accomplished using 85:15-heptane/ethyl acetate. The product-containing fractions were combined and concentrated under reduced pressure, yielding 1.9 grams of sticky solid. The solid was recrystallized from hexane, yielding 1.7 grams of 1-methyl-3-(2,3,5-trichlorophenylmethyl)-6-trifluoromethyluracil, mp 127.5°–129.5° C. The NMR spectrum was consistent with the proposed structure.

EXAMPLE 2

SYNTHESIS OF 3-(2,5-DICHLORO-3-METHOXYPHENYLMETHYL)-1-METHYL-6-TRIFLUOROMETHYLURACIL (COMPOUND 26)

Step A Synthesis of 3-amino-2,5-dichlorobenzoic acid as an intermediate

To a flask in which had been placed 47.20 grams (0.20 mole) of 2,5-dichloro-3-nitrobenzoic acid and 40.0 grams (0.326 mole) of granular tin were added, with good agitation, 200 mL of water and 200 mL of concentrated hydrochloric acid. The stirred reaction mixture was heated at 95° C. for 4.5 hours and at the conclusion of this period was poured over ice, causing a solid to form. This solid was removed by filtration and washed with water, then dissolved in ethyl acetate. This solution was washed three times with water and once with a saturated aqueous solution of sodium chloride. After being dried over anhydrous sodium sulfate and filtered, the solution was evaporated under reduced pressure to yield solid 3-amino-2,5-dichlorobenzoic acid, weighing 39.25 grams.

Step B Synthesis of 2,5-dichloro-3-iodobenzoic acid as an intermediate

In a flask 48.35 grams (0.191 mole) of iodine was dissolved in 90 mL of dimethyl sulfoxide. To this solution was added 29.47 grams (0.286 mole) of tertiary butyl nitrite. A solution of 39.25 grams (0.191 mole) of 3-amino-2,5-dichlorobenzoic acid in 130 mL of dimethyl sulfoxide was added dropwise to the solution of iodine and butyl nitrite. During this addition the temperature rose from 20° C. to 50° C., at which temperature the addition was stopped until the reaction mixture had cooled to 35° C. The addition was then completed. When the addition was complete, the reaction mixture was stirred for approximately 16 hours, then poured into water, and this mixture was extracted with ethyl acetate. The extracts were combined and washed with an aqueous solution of sodium hydrogen sulfate and finally with water. The combined extracts were dried over anhydrous sodium sulfate and filtered. The solvent was evaporated from the filtrate under reduced pressure, yielding 51.34 grams of 2,5-dichloro-3-iodobenzoic acid as a solid.

Step C Synthesis of 2,5-dichloro-3-hydroxybenzoic acid as an intermediate

To a flask containing 1100 mL of water was added 97.20 grams (2.43 moles) of sodium hydroxide. When the sodium hydroxide was completely dissolved, 51.34 grams (0.162 mole) of 2,5-dichloro-3-iodobenzoic acid was added, turning the solution black. To this black solution was added 26.29 grams (0.105 mole) of copper-(II) sulfate pentahydrate. The reaction mixture was heated to 100° C. and maintained at this temperature for three hours. At the-conclusion of this period, the reaction mixture was cooled in an icewater bath and then acidified with concentrated hydrochloric acid. This mixture was extracted with ethyl acetate, and the extract was washed four times with water and once with a saturated aqueous solution of sodium chloride. The extract was dried over anhydrous sodium sulfate and filtered. The solvent was evaporated from the filtrate under reduced pressure, leaving 21.79 grams of 2,5-dichloro-3-hydroxybenzoic acid as a black solid.

Step D Synthesis of methyl 2,5-dichloro-3-methoxybenzoate as an intermediate

In a flask 21.79 grams (0.105 mole) of 2,5-dichloro-3-hydroxybenzoic acid was dissolved in approximately 500 mL of acetone, and 58.60 grams (0.316 mole) of potassium carbonate and 50.92 grams (0.368 mole) of dimethyl sulfate were added. This mixture was heated at reflux for four hours, after which it was cooled and filtered. The filtrate was evaporated under reduced pressure, leaving a residue, which was taken up in ethyl acetate and water. The ethyl acetate layer was separated and washed three times with water and once with a saturated aqueous solution of sodium chloride. The solvent was then evaporated from the ethyl acetate solution, leaving a purple residue. This residue was distilled in a short path distillation apparatus, yielding the following fractions:

| Fraction | Oil Bath °C. | Head Temp °C. | Pressure mm Hg | Weight grams |
| --- | --- | --- | --- | --- |
| 1 | 77–84 | 38–26 | 0.04 | 3.48 |
| 2 | 115–146 | 27–105 | 0.04 | 0.11 |
| 3 | 146–180 | 105–125 | 0.04 | 17.26 |

NMR analysis of Fraction 3 was consistent with it being methyl 2,5-dichloro-3-methoxybenzoate contaminated with some dimethyl sulfate.

Step E Synthesis of 2,5-dichloro-3-methoxyphenylmethanol as an intermediate

To a suspension of 3.62 grams (0.095 mole) of lithium aluminum hydride in 200 mL of diethyl ether was added dropwise at a rate to maintain a gentle reflux a solution of 17.26 grams (0.073 mole) of methyl 2,5-dichloro-3- methoxybenzoate in 70 mL of diethyl ether. Upon completion of addition, the reaction mixture was refluxed for an additional three hours after which it was cooled in an ice-water bath. Very carefully, 5.5 mL of water, 4.5 mL of a 20% aqueous solution of sodium hydroxide, and 12 mL of water were added sequentially to the vigorously stirred reaction mixture. The reaction mixture was filtered through Celite® filter aid, which removed the finely divided precipitate. The solvent was then evaporated from the filtrate under reduced pressure, leaving an oil as the residue. The oil was dissolved in ethyl acetate, and this solution was washed twice with water and once with a saturated aqueous solution of sodium chloride. After being dried over anhydrous sodium sulfate, the solvent was evaporated under reduced pressure, leaving 14.22 grams of 2,5-dichloro-3-methoxyphenylmethanol as a yellow oil. This oil solidified on standing, yielding solid 2,5-dichloro-3-methoxyphenylmethanol, m.p. 58°–64° C. The NMR spectrum was consistent with the proposed structure.

Step F Synthesis of 2,5-dichloro-3-methoxyphenylmethyl bromide as an intermediate By the method of Example 1, Step B, 13.95 grams (0.0674 mole) of 2,5-dichloro-3-methoxyphenylmethanol and 7.295 grams (0.270 mole) of phosphorus tribromide were reacted in toluene, yielding 15.76 grams of 2,5-dichloro-3-methoxyphenylmethyl bromide as an oil. The NMR spectrum was consistent with the proposed structure.

Step G Synthesis of 2,5-dichloro-3-methoxyphenylacetonitrile as an intermediate

By the method of Example 1, Step C, 15.40 grams (0.057 mole) of 2,5-dichloro-3-methoxyphenylmethyl bromide and 3.63 grams (0.074 mole) of sodium cyanide were reacted in 70 mL of water and 65 mL of methanol, yielding 12.0 g of 2,5-dichloro-3-methoxyphenylacetonitrile as an oil that solidified on standing, m.p. 53°–57° C. The NMR and IR spectra were consistent with the proposed structure.

Step H Synthesis of 2,5-dichloro-3-methoxyphenylacetic acid as an intermediate

By the method of Example 1, Step D, 11.71 grams (0.054 mole) of 2,5-dichloro-3-methoxyphenylacetonitrile and 100 mL of concentrated sulfuric acid were reacted in 100 mL of water, yielding 11.21 grams of 2,5-dichloro-3-methoxyphenylacetic acid as a brown solid. The NMR spectrum was consistent with the proposed structure.

Step I Synthesis of 2,5-dichloro-3-methoxyphenylacetyl chloride as an intermediate By the method of Example 1, Step E, 10.92 grams (0.046 mole) of 2,5-dichloro-3-methoxyphenylacetic acid and 40 mL of thionyl chloride were reacted in approximately 200 mL of carbon tetrachloride, yielding 11.92 grams of 2,5-dichloro-3-methoxyphenylacetyl chloride as a black oil. The IR spectrum was consistent with the proposed structure.

Step J Synthesis of 2,5-dichloro-3-methoxyphenylmethyl isocyanate as an intermediate By the method of Example 1, Step F, 11.58 grams (0.046 mole) of 2,5-dichloro-3-methoxyphenylacetyl chloride and 5.53 grams (0.048 mole) of azidotrimethylsilane were reacted in 110 mL of toluene in the presence of five drops of triethylamine, yielding 11.72 grams of 2,5-dichloro-3-methoxyphenylmethyl isocyanate as a black oil. The IR spectrum indicated the presence of an isocyanate group. This material was used without further analysis or purification in the next reaction.

Step K Synthesis of 3-(2,5-dichloro-3-methoxyphenylmethyl)-6-trifluoromethyluracil as an intermediate By the method of Example 1, Step G, 10.61 grams (0.046 mole) of 2,5-dichloro-3-methoxyphenylmethyl isocyanate, 1.21 grams (0.050 mole) of sodium hydride, and 8.37 grams (0.046 mole) of ethyl 3-amino-4,4,4-trifluoro-2-butenoate in 80 mL of N,N-dimethylformamide, yielding 9.18 grams of 3-(2,5-dichloro-3-methoxyphenylmethyl)-6-trifluoromethyluracil as a solid, m.p. >220° C. The NMR spectrum was consistent with the proposed structure.

Step L Synthesis of 3-(2,5-dichloro-3-methoxyphenylmethyl)-1-methyl-6-trifluoromethyluracil (Compound 26)

By the method of Example 1, Step H, 8.95 grams (0.024 mole) of 3-(2,5-dichloro-3-methoxyphenylmethyl)-6-trifluoromethyluracil, 5.03 grams (0.036 mole) of dimethyl sulfate, and 8.99 grams (0.048 mole) of potassium carbonate were reacted in 800 mL of acetone, yielding 6.0 grams of 3-(2,5-dichloro-3-methoxyphenylmethyl)-1-methyl-6-trifluoromethyluracil as a viscous, yellow oil, which became a glass upon cooling. This glass crystallized after standing for a period of time, m.p. 117°–123° C. The NMR spectrum was consistent with the proposed structure.

EXAMPLE 31

SYNTHESIS OF 3-(2,3-DICHLORO-5-IODOPHENYLMETHYL)-1-METHYL-6-TRIFLUOROMETHYLURACIL (COMPOUND 58)

Step A Synthesis of a mixture of 2,3-dichloro-5-nitrobenzoic acid and 2,3-dichloro-4-nitrobenzoic acid as intermediates In a flask 50.05 grams (0.262 mole) of 2,3-dichlorobenzoic acid was dissolved in 500 mL of concentrated sulfuric acid, and the resulting solution was cooled to 4° C. Slowly, 40 mL of concentrated nitric acid was added to the solution while the temperature was maintained below 10° C. Upon completion of addition, the reaction mixture was stirred at 4° C. for two hours and then allowed to warm to ambient temperature, at which it was stirred for approximately 16 hours. At the conclusion of this period, the reaction mixture was poured over ice. The precipitate that formed was filtered from the mixture and was washed three times with 200 mL of cold water. The solid was then dissolved in 1200 mL of ethyl acetate, and the resulting solution was washed in succession three times with water and once with a saturated aqueous solution of sodium chloride. The solution was then dried over anhydrous sodium sulfate and filtered. The solvent was evaporated from the filtrate under reduced pressure, leaving 48.80 grams of solid residue. This solid was dissolved in a warm mixture of hexane and ethyl acetate and then allowed to cool and crystallize. A solid weighing 15.81 grams was recovered by filtration. The NMR spectrum of this solid indicated that it was 2,3-dichloro-5-nitrobenzoic acid. The filtrate was then evaporated under reduced pressure, yielding 30.65 grams of a solid which was shown by NMR spectroscopy to be a mixture of 2,3-dichloro-5-nitrobenzoic acid and 2,3-dichloro-4-nitrobenzoic acid. This reaction was repeated several times.

Step B Synthesis of 2,3-dichloro-5-nitrophenylmethanol as an intermediate

In a flask under a nitrogen atmosphere, 81.60 grams (0.346 mole) of 2,3-dichloro-5-nitrobenzoic acid was dissolved in 325 mL of tetrahydrofuran, and this solution was cooled to below 10° C. To this solution was slowly added 400 mL (0.400 mole) of a 1.0M solution of borane-tetrahydrofuran complex in tetrahydrofuran. Upon completion of addition, the temperature of the reaction mixture was allowed to rise to ambient conditions, at which it was stirred for about 20 hours. At the conclusion of this period, 40 mL of water was slowly added to the reaction mixture. This was followed by the addition of 220 mL of 10% aqueous hydrochloric acid. Addition of the water had caused the mixture to become cloudy, but addition of the acid restored the clarity of the solution. The solvent was concentrated under reduced pressure, leaving a residue which was then dissolved in approximately 1500 mL of ethyl acetate. This solution was washed in succession three times with water, four times with an aqueous solution of sodium bicarbonate, once with water, and finally with a saturated aqueous solution of sodium chloride. The solution was dried over anhydrous sodium sulfate and filtered. The solvent was evaporated from the filtrate under reduced pressure, leaving 61.90 grams of 2,3-dichloro-5-nitrophenylmethanol as a solid residue. The NMR spectrum was consistent with the proposed structure.

Step C Synthesis of 2,3-dichloro-5-nitrophenylmethyl bromide as an intermediate

By the method of Example 1, Step B, 61.90 grams (0.279 mole) of 2,3-dichloro-5-nitrophenylmethanol and 26.41 grams (0.098 mole) of phosphorus tribromide were reacted in 800 mL of toluene, yielding 64.38 grams of 2,3-dichloro-5-nitrophenylmethyl bromide as a golden oil which solidified upon standing. The NMR spectrum was consistent with the proposed structure.

Step D Synthesis of 2,3-dichloro-5-nitrophenylacetonitrile as an intermediate

By the method of Example 1, Step C, 64.38 grams (0.226 mole) of 2,3-dichloro-5-nitrophenylmethyl bromide and 14.4 grams (0.294 mole) of sodium cyanide were reacted in 600 mL of water and 500 mL of methanol, yielding 47.43 grams of a dull, green solid. The NMR spectrum indicated that this solid was composed of a mixture of 2,3-dichloro-5-nitrophenylacetonitrile (80%) and 2,3-dichloro-5-nitrophenylmethyl bromide (20%).

Step E Synthesis of 2,3-dichloro-5-nitrophenylacetic acid as an intermediate

By the method of Example 1, Step D, 47.43 grams (0.205 mole) of the mixture of 2,3-dichloro-5-nitrophenylacetonitrile (80%) and 2,3-dichloro-5-nitrobenzyl bromide (20%) (Step D) and 250 mL of concentrated sulfuric acid were reacted in 250 mL of water, yielding 18.27 grams of 2,3-dichloro-5-nitrophenylacetic acid as a solid. The NMR spectrum was consistent with the proposed structure.

Step F Synthesis of 2,3-dichloro-5-nitrophenylacetyl chloride as an intermediate By the method of Example 1, Step E, 18.27 grams (0.073 mole) of 2,3-dichloro-5-nitrophenylacetic acid and 80 mL of thionyl chloride were reacted in 400 mL of carbon tetrachloride, yielding 20.90 grams of 2,3-dichloro-5-nitrophenylacetyl chloride. The NMR spectrum was consistent with the proposed structure.

Step G Synthesis of 2,3-dichloro-5-nitrophenylmethyl isocyanate as an intermediate By the method of Example 1, Step F, 20.90 grams (0.078 mole) of 2,3-dichloro-5-nitrophenylacetyl chloride and 9.86 grams (0.086 mole) of azidotrimethylsilane were reacted in 200 mL of toluene in the presence of seven drops of triethylamine, yielding 19.67 grams of 2,3-dichloro-5-nitrophenylmethyl isocyanate as a dark brown oil. The NMR spectrum was consistent with the proposed structure. The IR spectrum indicated that isonitrile was also present.

Step H Synthesis of 3-(2,3-dichloro-5-nitrophenylmethyl)-6-trifluoromethyluracil as an intermediate By the method of Example 1, Step G, 19.67 grams (0.080 mole) of 2,3-dichloro-5-nitrophenylmethyl isocyanate, 2.102 grams (0.088 mole) of sodium hydride, and 14.59 grams (0.080 mole) of ethyl 3-amino-4,4,4-trifluoro-2-butenoate were reacted in 80 mL of N,N-dimethylformamide, yielding 17.14 grams of 3-(2,3-dichloro-5-nitrophenylmethyl)-6-trifluoromethyluracil as a brown solid. The NMR spectrum was consistent with the proposed structure. This reaction was repeated.

Step I Synthesis of 3-(2,3-dichloro-5-nitrophenylmethyl)-1-methyl-6-trifluoromethyluracil as an intermediate By the method of Example 1, Step H, 24.5 grams (0.064 mole) of 3-(2,3-dichloro-5-nitrophenylmethyl)-6-trifluoromethyluracil, 12.07 grams (0.096 mole) of dimethyl sulfate, and 17.64 grams (0.127 mole) of potassium carbonate were reacted in 300 mL of acetone, yielding 5.30 grams of 3-(2,3-dichloro-5-nitrophenylmethyl)-1-methyl-6-trifluoromethyluracil as a bright yellow solid. The NMR spectrum was consistent with the proposed structure.

Step J Synthesis of 3-(5-amino-2,3-dichlorophenylmethyl)-1-methyl-6-trifluoromethyluracil as an intermediate In flask were placed 7.47 grams (0.019 mole) of 3-(2,3-dichloro-5-nitrophenylmethyl)-1-methyl-6-trifluoromethyluracil and 5.68 grams (0.94 mole) of powdered iron in 115 mL of ethanol and 9 mL of water. Dropwise, 9.0 mL of concentrated hydrochloric acid was added to the reaction mixture. Upon completion of addition, the reaction mixture was heated to 65° C. and maintained at this temperature for three hours. After being cooled to ambient conditions, the reaction mixture was filtered through Celite filter aid, and the collected precipitate was washed several times with ethanol. The solid removed by filtration was then dissolved in ethyl acetate, and this solution was washed twice with a saturated aqueous solution of sodium chloride. The dark brown solution was dried over anhydrous sodium sulfate and filtered. The solvent was evaporated from the filtrate under reduced pressure, leaving 1.62 grams of 3-(5-amino-2,3-dichlorophenylmethyl)-1-methyl-6-trifluoromethyluracil as a solid. This reaction was repeated.

Step K Synthesis of 3-(2,3-dichloro-5-iodophenylmethyl)-1-methyl-6-trifluoromethyluracil (Compound 58)

By the method of Example 2, Step B, 2.67 grams (0.00725 mole) of 3-(5-amino-2,3-dichlorophenylmethyl)-1-methyl-6-trifluoromethyluracil, 1.84 grams (0.00725 mole) of iodine, and 1.12 grams (0.0109 mole) of tertiarybutyl nitrite were reacted in 10 mL of dimethyl sulfoxide, yielding 3.83 grams of 3-(2,3-dichloro-5-iodophenylmethyl)-1-methyl-6-trifluoromethyluracil as a light brown solid, m.p. 142°–144° C. The NMR and IR spectra were consistent with the proposed structure.

The compounds described in Table 1 were prepared by methods similar to those set forth above. Characterizing data for these compounds are given in Table 2.

HERBICIDAL ACTIVITY

The herbicides of this invention were tested for pre- and postemergence herbicidal activity using a variety of crops and weeds. The test plants included soybean (*Glycine max* var. Williams), field corn (*Zea mays* var. Agway 425X), wheat (*Triticum aestivum* var. Wheaton), morningglory (*Ipomoea lacunosa* or *Ipomoea hederacea*), velvetleaf (*Abutlion theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 8-12 days prior to the preemergence flats and were placed in a greenhouse and watered, thus allowing the seeds to germinate and the foliage to develop.

In both pre- and postemergence tests, a stock solution of the candidate herbicide was prepared by dissolving a predetermined weight of the compound in 20 mL of water/acetone (50/50) containing 0.5% v/v sorbitan monolaurate. Thus for an application rate of up to 3000 g/ha of herbicide, 0.27 g of candidate herbicide was dissolved in 20 mL of the aqueous acetone to prepare the stock solution. A portion (10 mL) was then diluted with water/acetone (50/50) to 45 mL, the volume required to correspond to a spray volume of 1000 L/ha. The remaining stock solution was then used to prepare solutions for lower application rates.

For the 0.3 kg/ha rate reported in Tables 3 and 4, 1.0 mL of stock solution was diluted with 44 mL of water/acetone (50/50) to 45 mL.

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 17-21 days the plants were examined and the phytotoxicity data were recorded.

Herbicidal activity data are given in Table 3 and Table 4 for various 3-(substituted-benzyl)-1-methyl-6-trifluoromethyluracils. Both compounds of the invention and closely related compounds are included to show the unpredictability and criticality of the substitution pattern of the phenyl ring required to give active herbicides in this class of compounds. The test compounds are identified by numbers which correspond to those in Table 1, where the numbers for particularly preferred compounds of the invention are underlined.

In view of the structural similarity of compounds disclosed in the references cited above to the compounds of the present invention, some showing that inferences that might seem obvious from the references do not apply to the compounds here claimed seems appropriate. The closest reference is U.S. Pat. No. 3,580,913, which, as noted above, would disclose the genus of the present compounds if it disclosed an alkyl substituent in the 1-position of the uracil. The reference provides for a substituted benzyl, inter alia, in the 3-position, disclosing an extensive list of possible substituents, including halo, alkyl, and alkoxy. Compound 5 is clearly within the scope of the disclosure of the reference and is the desmethyl analog of compound 4 of the invention. Comparison of the data for these two compounds in Tables 3 and 4 shows that reference compound 5 gives little or no control over the test species, while compound 4 gives complete control of eight of the ten species.

Similarly, the references generally do not suggest any criticality among any of the many possible suggested substituents, including halo, alkyl, and alkoxy, at any position. However, a comparison of compounds with methyl or methoxy groups (compounds 11, 12, and 13) with the corresponding chlorine compounds (compounds 9, 4, and 9, respectively) shows that in the genus here claimed the nature of the substituent is critical indeed. Even when the substituent is preferred, as in chlorine, the substitution pattern is critical. Thus, whereas for dichloro substitution the 2,3 compound (4) is outstanding, the 2,4, 2,5, and 2,6 compounds (6, 7, and 8, respectively) are far less active. In the trichloro series, the 2,3,5 and 2,3,4 compounds (14 and 18) are highly active, but the 2,3,6 compound (15) is inactive. The effect of substituents other than chloro is similarly unpredictable. For example, the two monochloro, cyano compounds (22 and 23) are inactive, whereas the two dichloro, cyano compounds (17 and 26) are both active. However, one (17) is much more active than the parent dichloro compound (7), while the other (26) is somewhat less active than the parent (4). In short, nothing in the references suggests or makes obvious the surprising criticality of the substitution patterns in the novel class of compounds here disclosed. Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Alabama, 1977. The rating system is as follows:

| Herbicide Rating System | | | |
| --- | --- | --- | --- |
| Rating Percent Control | Description of Main Categories | Crop Description | Weed Description |
| 0 | No effect | No crop reduction | No weed control |

| Herbicide Rating System | | | |
|---|---|---|---|
| Rating Percent Control | Description of Main Categories | Crop Description | Weed Description |
| 10 | | Slight discoloration or stunting or injury | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

Evaluation of Compound 14 against additional weeds and crops at a lower rate of application (31.3 g/ha) showed that several crops were significantly less affected by the herbicide than were a variety of weeds. In this test the crop species were cotton (*Gossypium hirsutum*) and peanut (*Arachis hypogaea*) in addition to corn and soybean. The undesired plant species were barnyardgrass (*Echinochloa crus-galli*), prickly sida (*Sida apinosa*), redroot pigweed *Amaranthus retroflexus*), lambsquarter (*Chenopodium album*), proso millet (*Panicum milaceum*), giant foxtail (*Setaria faberii*), Pennsylvania smartweed (*Polygonurn pennsylvanicum*), shattercane (*Sorghum bicolor*), large crabgrass (*Digitaria sanguinalis*), and broadleaf signalgrass (*Brachiaria platyphylla*) in addition to Johnsongrass, green foxtail, morningglory, and velvetleaf. The test procedure was identical to that described above, except that the spray volume corresponded to 187 L/ha, and application was preemergence only.

The results of this evaluation are given in Table 5. At the test rate, injury to corn and peanut was negligible, while cotton and soybean sustained only slight injury, not likely to be lasting. (Conclusions are based on the Herbicide Rating System shown above.) Of the fourteen weeds, seven were completely controlled, one was satisfactorily controlled, three were moderately controlled, and only one, morningglory, escaped significant control.

For herbicidal application the active compounds of the invention are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient. Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. A wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently additional wetting agent(s) and/or oil will be added to the tank mix for postemergence application to facilitate dispersion on the foliage and absorption by the plant.

Other useful formulations for herbicidal applications are emulsifiable concentrates (ECs), which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECS, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and the sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent(s), when used, normally comprises from 1 to 15% by weight of the composition.

Other useful formulations include suspensions of the active ingredient in a relatively non-volatile liquid such as water, corn oil, kerosene, propylene glycol, or other suitable liquid carrier.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granule are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful with the present herbicidal compounds. For use by the farmer on the field, the granular formulations, emulsifiable concentrates, flowable concentrates, solutions, etc., may be diluted with water to give a concentration of active ingredient in the range of, say, 0. 1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is, of course, employed; the amount may be as low as, e.g., about 10 to 100 g/ha, preferably about 30 to 60 g/ha. For field use, where there are losses of herbicide, higher application rates (e.g., four times the greenhouse testing rates mentioned above) may be employed. The active herbicidal compounds of this invention may be used in combination with other herbicides, e.g., they may be mixed with, say, a lesser, equal, or larger amount of a known herbicide such as aryloxyalkanoic acid herbicides such as (2,4-dichlorophenoxy)acetic acid (2,4-D), (4-chloro-2-methylphenoxy)acetic acid (MCPA), (+/−)-2-(4-chloro-2-methylphenoxy)propanoic acid (MCPP); urea herbicides, such as N,N-dimethyl-N'-[4-(1-methylethyl)phenyl]urea (isoproturon); imidazolinone herbicides, such as 2-[4,5-dihydro-4-methyl-4-( 1 -methylethyl)-5-oxo-1H-imidazol-2-yl]-3-pyridinecarboxylic acid (imazapyr), a reaction product comprising (+/−)-2-[4,5-dihydro-4-methyl-4-( 1 -methylethyl)-5-oxo-1H-imidazol-2-yl]-4-methylbenzoic acid and (+/−)-2-[4,5-dihydro-4-methyl-4-( 1 -methylethyl)-5-oxo-1H-imidazol-2-yl]-5-methylbenzoic acid (imazamethabenz), (+/−)-2-[4,5-dihydro-4-methyl-4-( 1 -methylethyl)-5-oxo-1H-imidazol-2-yl]-5-ethyl-3-pyridinecarboxylic acid (imazethapyr), and (+/−)-2-[4,5-dihydro-4-methyl-4-(1-methylethyl)-5-oxo-1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino]sulfonyl]-benzoic acid (chlorimuron), 2-chloro-N-[[(4-methoxy-6-methyl-1,3,5-triazin-2-yl)amino]carbonyl]benzenesulfonamide (chlorsulfuron), 2-[[[[(4,6-dimethoxy-2-pyrimidinyl)amino]carbonyl]amino]sulfonyl]methyl]benzoic acid (bensulfuron), 2-[[[[(4,6-dimethoxy-2-pyrimidinyl)amino]carbonyl]amino] -sulfonyl]-1-methyl-1H-pyrazol-4-carboxylic acid (pyrazosulfuron), 3-[[[[(4-methoxy-6-methyl- 1,3,5-triazin-2-yl)amino]carbonyl]amino]sulfonyl]-2-thiophenecarboxylic acid (thifensulfuron), and 2-(2-chloroethoxy)-N-[[(4-methoxy-6-methyl- 1,3,5-triazin-2-yl)amino]carbonyl]benzenesulfonamide (triasulfuron); 2-(4-aryloxyphenoxy)alkanoic acid herbicides, such as (+/−)-2-[4-[(6-chloro-2-benzoxazolyl)oxy]phenoxy]propanoic acid (fenoxaprop), (+/−) -2-[4-[[5-(trifluoromethyl)-2-pyridinyl]oxy]phenoxy]propanoic acid (fluazifop), ( +/−)-2-[4-(6-chloro-2-quinoxalinyl)oxy]phenoxy]-propanoic acid (quizalofop), and ( +/−)-2-[-(2,4-dichlorophenoxy)phenoxy]propanoic acid (diclofop); benzothiadiazinone herbicides, such as 3-(1-methylethyl)-1H-2,1,3-benzothiadiazin-4( 3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

Herbicidal 3-(Substituted-arylmethyl)-1-substituted-6-trifluoromethyluracils

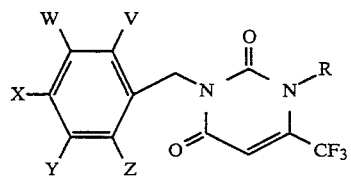

| Cmpd. No. | R | V | W | X | Y | Z |
|---|---|---|---|---|---|---|
| 1 | —CH₃ | H | Cl | H | H | H |
| 2 | —CH₃ | H | H | Cl | H | H |
| 3 | —CH₃ | F | Cl | H | H | H |
| 4 | —CH₃ | Cl | Cl | H | H | H |
| 5 | H | Cl | Cl | H | H | H |
| 6 | —CH₃ | Cl | H | Cl | H | H |
| 7 | —CH₃ | Cl | H | H | Cl | H |
| 8 | —CH₃ | Cl | H | H | H | Cl |
| 9 | —CH₃ | H | Cl | H | Cl | H |
| 10 | —CH₃ | H | Cl | Cl | H | H |
| 11 | —CH₃ | H | —CH₃ | H | —CH₃ | H |
| 12 | —CH₃ | —OCH₃ | —OCH₃ | H | H | H |
| 13 | —CH₃ | H | —OCH₃ | H | —OCH₃ | H |
| 14 | —CH₃ | Cl | Cl | H | Cl | H |
| 15 | —CH₃ | Cl | Cl | H | H | Cl |
| 16 | —CH₃ | Cl | I | H | Cl | H |
| 17 | —CH₃ | Cl | —CN | H | Cl | H |
| 18 | —CH₃ | Cl | Cl | Cl | H | H |
| 19 | —CH₃ | Cl | —OMe | H | Cl | H |
| 20 | —CH₃ | Cl | —C(O)NHC₂H₅ | H | Cl | H |
| 21 | —CH₃ | Cl | H | H | I | H |
| 22 | —CH₃ | Cl | H | H | —CN | H |
| 23 | —CH₃ | I | H | H | Cl | H |
| 24 | —CH₃ | —CN | H | H | Cl | H |
| 25 | —CH₃ | Cl | Cl | H | I | H |
| 26 | —CH₃ | Cl | Cl | H | —CN | H |
| 27 | —CH₃ | Cl | Cl | H | —CO₂H | H |
| 28 | —CH₃ | Cl | Cl | H | —C(O)NH(C₂H₅) | H |
| 29 | —CH₃ | Cl | —OCH₂C≡CH | H | Cl | H |

TABLE 2

Characterizing Data

| Compound No. | MP (°C.) | Compound No. | MP (°C.) |
|---|---|---|---|
| 1 | 79–81 | 16 | 173–175.5 |
| 2 | 78–81 | 17 | 198–200 |
| 3 | 85–87 | 18 | 155–157 |
| 4 | 119–122 | 19 | 117–123 |
| 5 | 204–206 | 20 | 200–206 |
| 6 | 102–103.5 | 21 | 122–125 |
| 7 | 149.5–152 | 22 | 203.5–205.5 |
| 8 | 129–131 | 23 | 158–160 |
| 9 | oil | 24 | 176–179 |
| 10 | 118.5–120 | 25 | 142–144 |
| 11 | 88–90 | 26 | >200 |
| 12 | 90–91 | 27 | >200 |
| 13 | 92–95 | 28 | 124–128 |
| 14 | 127.5–129.5 | 29 | 139–144 |
| 15 | 129–133.5 | | |

TABLE 3

PREEMERGENCE HERBICIDAL ACTIVITY (% CONTROL)

| Compound No. | 1 | 2 | 3 | 4 |
|---|---|---|---|---|
| Rate (kg/ha) | 0.3 | 0.3 | 0.3 | 0.3 |
| Species | | | | |
| Soybean | 0 | 0 | 30 | 100 |
| Wheat | 40 | 30 | 80 | 80 |
| Corn | 85 | 80 | 95 | 100 |
| Velvetleaf | 100 | 100 | 100 | 100 |
| Morningglory | 0 | 10 | 100 | 100 |
| Chickweed | 60 | 100 | 100 | 100 |
| Cocklebur | 40 | 0 | 30 | 95 |
| Blackgrass | 50 | 75 | 100 | 100 |
| Green foxtail | 100 | 100 | 100 | 100 |
| Johnsongrass | 80 | 80 | 95 | 100 |
| Compound No. | 5 | 6 | 7 | 8 |
| Rate (kg/ha) | 0.3 | 0.3 | 0.3 | 0.3 |
| Species | | | | |
| Soybean | 15 | 10 | 50 | 0 |
| Wheat | 0 | 10 | 20 | 0 |
| Corn | 0 | 20 | 10 | 0 |
| Velvetleaf | 0 | 85 | 95 | 0 |
| Morningglory | 0 | 40 | 90 | 0 |
| Chickweed | 10 | 50 | 10 | 0 |
| Cocklebur | 0 | 0 | 10 | 0 |
| Blackgrass | 10 | 20 | 10 | 0 |
| Green foxtail | 10 | 100 | 100 | 0 |
| Johnsongrass | 10 | 40 | 75 | 0 |
| Compound No. | 9 | 10 | 11 | 12 |
| Rate (kg/ha) | 0.3 | 0.3 | 0.3 | 0.3 |
| Species | | | | |
| Soybean | 80 | 10 | 0 | 0 |
| Wheat | 40 | 20 | 10 | 0 |
| Corn | 30 | 50 | 0 | 0 |
| Velvetleaf | 100 | 100 | 95 | 0 |
| Morningglory | 100 | 80 | 10 | 0 |
| Chickweed | 100 | 100 | 0 | ND |
| Cocklebur | 20 | 0 | 0 | 0 |
| Blackgrass | 70 | 90 | 0 | 0 |
| Green foxtail | 100 | 100 | 10 | 0 |
| Johnsongrass | 95 | 90 | 40 | 0 |
| Compound No. | 13 | 14 | 15 | 16 |
| Rate (kg/ha) | 0.3 | 0.3 | 0.3 | 0.3 |
| Species | | | | |

TABLE 3-continued

PREEMERGENCE HERBICIDAL ACTIVITY (% CONTROL)

| Species | | | | |
|---|---|---|---|---|
| Soybean | 50 | 95* | 0 | 50 |
| Wheat | 0 | 95* | 0 | 20 |
| Corn | 60 | 85* | 0 | 20 |
| Velvetleaf | 95 | 100* | 0 | 100 |
| Morningglory | 20 | 100* | 0 | 100 |
| Chickweed | ND | 100* | 0 | 100 |
| Cocklebur | 10 | 90* | 0 | 30 |
| Blackgrass | 20 | 100* | 0 | 95 |
| Green foxtail | 80 | 100* | 0 | 100 |
| Johnsongrass | 50 | 100* | 0 | 60 |

| Compound No. | 17 | 18 | 19 | 20 |
|---|---|---|---|---|
| Rate (kg/ha) | 0.3 | 0.3 | 0.3 | 0.3 |

| Species | | | | |
|---|---|---|---|---|
| Soybean | 100 | 100 | 0 | 20 |
| Wheat | 60 | 70 | 0 | 20 |
| Corn | 80 | 60 | 90 | 40 |
| Velvetleaf | 100 | 100 | 100 | 100 |
| Morningglory | 100 | 100 | 100 | 40 |
| Chickweed | 100 | 100 | 100 | 100 |
| Cocklebur | 90 | 50 | 70 | 0 |
| Blackgrass | 100 | 95 | 100 | 60 |
| Green foxtail | 100 | 100 | 100 | 100 |
| Johnsongrass | 100 | 100 | 95 | 50 |

| Compound No. | 21 | 22 | 23 | 24 |
|---|---|---|---|---|
| Rate (kg/ha) | 0.3 | 0.3 | 0.3 | 0.3 |

| Species | | | | |
|---|---|---|---|---|
| Soybean | 0 | 10 | 0 | ND |
| Wheat | 0 | 0 | 0 | 0 |
| Corn | 10 | 0 | 0 | 0 |
| Velvetleaf | 30 | 10 | 40 | 0 |
| Morningglory | 0 | 10 | 0 | 0 |
| Chickweed | 10 | 10 | 0 | ND |
| Cocklebur | 0 | 0 | 0 | 0 |
| Blackgrass | 10 | 0 | 0 | 0 |
| Green foxtail | 70 | 50 | 100 | 10 |
| Johnsongrass | 20 | 10 | 60 | 40 |

| Compound No. | 25 | 26 | 27 | 28 | 29 |
|---|---|---|---|---|---|
| Rate (kg/ha) | 0.3 | 0.3 | 0.3 | 0.3 | 0.3 |

| Species | | | | | |
|---|---|---|---|---|---|
| Soybean | 100 | 100 | 10 | 100 | 10 |
| Wheat | 70 | 50 | 0 | 60 | 0 |
| Corn | 95 | 80 | 40 | 80 | 50 |
| Velvetleaf | 100 | 100 | 100 | 100 | 100 |
| Morningglory | 100 | 100 | 50 | 100 | 85 |
| Chickweed | 100 | 100 | 100 | 100 | 100 |
| Cocklebur | 100 | 60 | 0 | 60 | 0 |
| Blackgrass | 100 | 70 | 30 | 100 | 70 |
| Green foxtail | 100 | 100 | 100 | 100 | 100 |
| Johnsongrass | 100 | 95 | 70 | 100 | 90 |

*Average of three results rounded to the next lower number ending in 0 or 5

TABLE 4

POSTEMERGENCE HERBICIDAL ACTIVITY (% CONTROL)

| Compound No. | 1 | 2 | 3 | 4 |
|---|---|---|---|---|
| Rate (kg/ha) | 0.3 | 0.3 | 0.3 | 0.3 |

| Species | | | | |
|---|---|---|---|---|
| Soybean | 20 | 30 | 80 | 95 |
| Wheat | 0 | 0 | 30 | 60 |
| Corn | 30 | 20 | 80 | 100 |
| Velvetleaf | 100 | 100 | 100 | 100 |
| Morningglory | 100 | 100 | 100 | 100 |
| Chickweed | 10 | 100 | 100 | 100 |
| Cocklebur | 60 | 40 | 75 | 100 |
| Blackgrass | 0 | 0 | 70 | 100 |
| Green foxtail | 30 | 95 | 75 | 100 |
| Johnsongrass | 30 | 10 | 90 | 100 |

| Compound No. | 5 | 6 | 7 | 8 |
|---|---|---|---|---|
| Rate (kg/ha) | 0.3 | 0.3 | 0.3 | 0.3 |

| Species | | | | |
|---|---|---|---|---|
| Soybean | 0 | 60 | 60 | 0 |
| Wheat | 0 | 0 | 0 | 0 |

TABLE 4-continued

POSTEMERGENCE HERBICIDAL ACTIVITY (% CONTROL)

| Corn | 0 | 60 | 30 | 0 |
|---|---|---|---|---|
| Velvetleaf | 0 | 100 | 100 | 0 |
| Morningglory | 10 | 80 | 90 | 0 |
| Chickweed | 0 | 20 | 80 | 0 |
| Cocklebur | 0 | 40 | 10 | 0 |
| Blackgrass | 0 | 0 | 0 | 0 |
| Green foxtail | 10 | 40 | 90 | 0 |
| Johnsongrass | 0 | 30 | 60 | 0 |

| Compound No. | 9 | 10 | 11 | 12 |
|---|---|---|---|---|
| Rate (kg/ha) | 0.3 | 0.3 | 0.3 | 0.3 |

| Species | | | | |
|---|---|---|---|---|
| Soybean | 95 | 30 | 80 | 0 |
| Wheat | 30 | 0 | 0 | 0 |
| Corn | 70 | 60 | 40 | 0 |
| Velvetleaf | 100 | 100 | 95 | 0 |
| Morningglory | 100 | 100 | 40 | 0 |
| Chickweed | 100 | 100 | 0 | 0 |
| Cocklebur | 100 | 100 | 0 | 0 |
| Blackgrass | 10 | 30 | 0 | 0 |
| Green foxtail | 90 | 95 | 70 | 0 |
| Johnsongrass | 95 | 90 | 50 | 0 |

| Compound No. | 13 | 14 | 15 | 16 |
|---|---|---|---|---|
| Rate (kg/ha) | 0.3 | 0.3 | 0.3 | 0.3 |

| Species | | | | |
|---|---|---|---|---|
| Soybean | 80 | 95* | 0 | 95 |
| Wheat | 10 | 95* | 0 | 40 |
| Corn | 30 | 90* | 0 | 100 |
| Velvetleaf | 95 | 100* | 0 | 100 |
| Morningglory | 90 | 100** | 0 | 100 |
| Chickweed | 100 | 100* | 0 | 100 |
| Cocklebur | 20 | 100* | 0 | 100 |
| Blackgrass | 0 | 100* | 0 | 100 |
| Green foxtail | 20 | 100* | 0 | 100 |
| Johnsongrass | 10 | 100* | 0 | 80 |

| Compound No. | 17 | 18 | 19 | 20 |
|---|---|---|---|---|
| Rate (kg/ha) | 0.3 | 0.3 | 0.3 | 0.3 |

| Species | | | | |
|---|---|---|---|---|
| Soybean | 95 | 95 | 60 | 95 |
| Wheat | 50 | 80 | 0 | 20 |
| Corn | 80 | 95 | 80 | 50 |
| Velvetleaf | 100 | 100 | 100 | 100 |
| Morningglory | 100 | ND | 90 | 100 |
| Chickweed | 100 | 100 | 100 | 100 |
| Cocklebur | 100 | 100 | 100 | 100 |
| Blackgrass | 100 | 100 | 100 | 20 |
| Green foxtail | 100 | 100 | 100 | 40 |
| Johnsongrass | 100 | 100 | 95 | 0 |

| Compound No. | 21 | 22 | 23 | 24 |
|---|---|---|---|---|
| Rate (kg/ha) | 0.3 | 0.3 | 0.3 | 0.3 |

| Species | | | | |
|---|---|---|---|---|
| Soybean | 80 | 30 | 70 | 20 |
| Wheat | 0 | 0 | 0 | 0 |
| Corn | 40 | 20 | 40 | 0 |
| Velvetleaf | 100 | 20 | 100 | 50 |
| Morningglory | 50 | 0 | 30 | 30 |
| Chickweed | 90 | 0 | ND | 0 |
| Cocklebur | 100 | 0 | 70 | 0 |
| Blackgrass | 20 | 0 | 0 | 0 |
| Green foxtail | 50 | 10 | 60 | ND |
| Johnsongrass | 60 | 0 | 40 | 0 |

| Compound No. | 25 | 26 | 27 | 28 | 29 |
|---|---|---|---|---|---|
| Rate (kg/ha) | 0.3 | 0.3 | 0.3 | 0.3 | 0.3 |

| Species | | | | | |
|---|---|---|---|---|---|
| Soybean | 95 | 95 | 70 | 70 | 40 |
| Wheat | 70 | 40 | 40 | 60 | 0 |
| Corn | 70 | 70 | 80 | 90 | 70 |
| Velvetleaf | 100 | 100 | 100 | 100 | 100 |
| Morningglory | 100 | 100 | 100 | 100 | 85 |
| Chickweed | 100 | 100 | 100 | 100 | 100 |
| Cocklebur | 100 | 100 | 100 | 90 | 90 |
| Blackgrass | 95 | 60 | 50 | 100 | 20 |
| Green foxtail | 100 | 100 | 100 | 100 | 95 |

TABLE 4-continued

POSTEMERGENCE HERBICIDAL ACTIVITY
(% CONTROL)

| Johnsongrass | 95 | 90 | 70 | 90 | 60 |

*Average of three results rounded to the next lower number ending on 0 or 5
**Average of two results rounded to the next lower number ending in 0 or 5

TABLE 5

| (Preemergence Herbicidal Evaluation of Compound 14) | |
|---|---|
| Species | Percent Control* |
| Corn | 5 |
| Soybean | 25 |
| Barnyardgrass | 85 |
| Johnsongrass | 65 |
| Green foxtail | 100 |
| Morningglory | 15 |
| Velvetleaf | 65 |
| Cotton | 25 |
| Prickly sida | 100 |
| Redroot pigweed | 100 |
| Lambsquarters | 100 |
| Proso millet | 55 |
| Giant foxtail | 100 |
| Pennsylvania smartweed | 100 |
| Shattercane | 55 |
| Large crabgrass | 100 |
| Broadleaf signalgrass | 55 |
| Peanut | 5 |

*Average of three results rounded to the nearest number ending in 0 or 5

I claim:
1. A compound of the formula

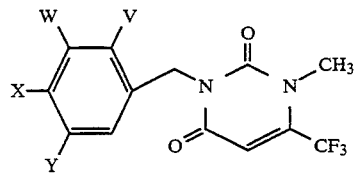

in which V is hydrogen or halogen;
W is hydrogen, halogen, lower alkoxy, lower alkylaminocarbonyl, propargyloxy, or cyano;
X is hydrogen or chlorine; and
Y is hydrogen, halogen, cyano, lower alkylaminocarbonyl, or carboxy, in which lower means having 1 to 3 carbon atoms, and with the proviso that when Y is other than hydrogen or chlorine, V and W are each chlorine, and when W is other than hydrogen or chlorine, V and Y are each chlorine.

2. A compound of claim 1 in which halogen is chlorine or iodine, and lower means having 1 to 2 carbon atoms.

3. A compound of claim 2 in which V is chlorine and Y is hydrogen.

4. The compound of claim 3 in which X is hydrogen and W is chlorine.

5. The compound of claim 3 in which X and W are each chlorine.

6. A compound of claim 2 in which V and Y are each chlorine, and X is hydrogen.

7. The compound of claim 6 in which W is chlorine.

8. The compound of claim 6 in which W is iodine.

9. The compound of claim 6 in which W is cyano.

10. The compound of claim 6 in which W is methoxy.

11. The compound of claim 6 in which W is propargyloxy.

12. The compound of claim 6 in which W is ethylaminocarbonyl.

13. A compound of claim 2 in which V is hydrogen, and W, X, and Y, are independently hydrogen or chlorine.

14. The compound of claim 13 in which W and X are chlorine, and Y is hydrogen.

15. The compound of claim 13 in which W and Y are chlorine, and X is hydrogen.

16. A compound of claim 2 in which V and W are each chlorine, X is hydrogen, and Y is iodine, cyano, carboxy, or ethylaminocarbonyl.

17. The compound of claim 16 in which Y is iodine.

18. The compound of claim 16 in which Y is cyano.

19. The compound of claim 16 in which Y is carboxy.

20. The compound of claim 16 in which Y is ethylaminocarbonyl.

21. A herbicidal composition comprising an herbicidally effective amount of a compound of claim 1 in admixture with an agriculturally acceptable carrier.

22. The method of controlling undesired plant growth which comprises applying to the locus where control is desired a herbicidally effective amount of a composition of claim 21.

23. The method of controlling undesired plant growth in a crop selected from cotton, corn, peanuts, and soybeans which comprises applying preemergence to the crop, at a rate between 0.035 and 0.140 kg/ha, a composition of claim 21.

* * * * *